Figure 1:
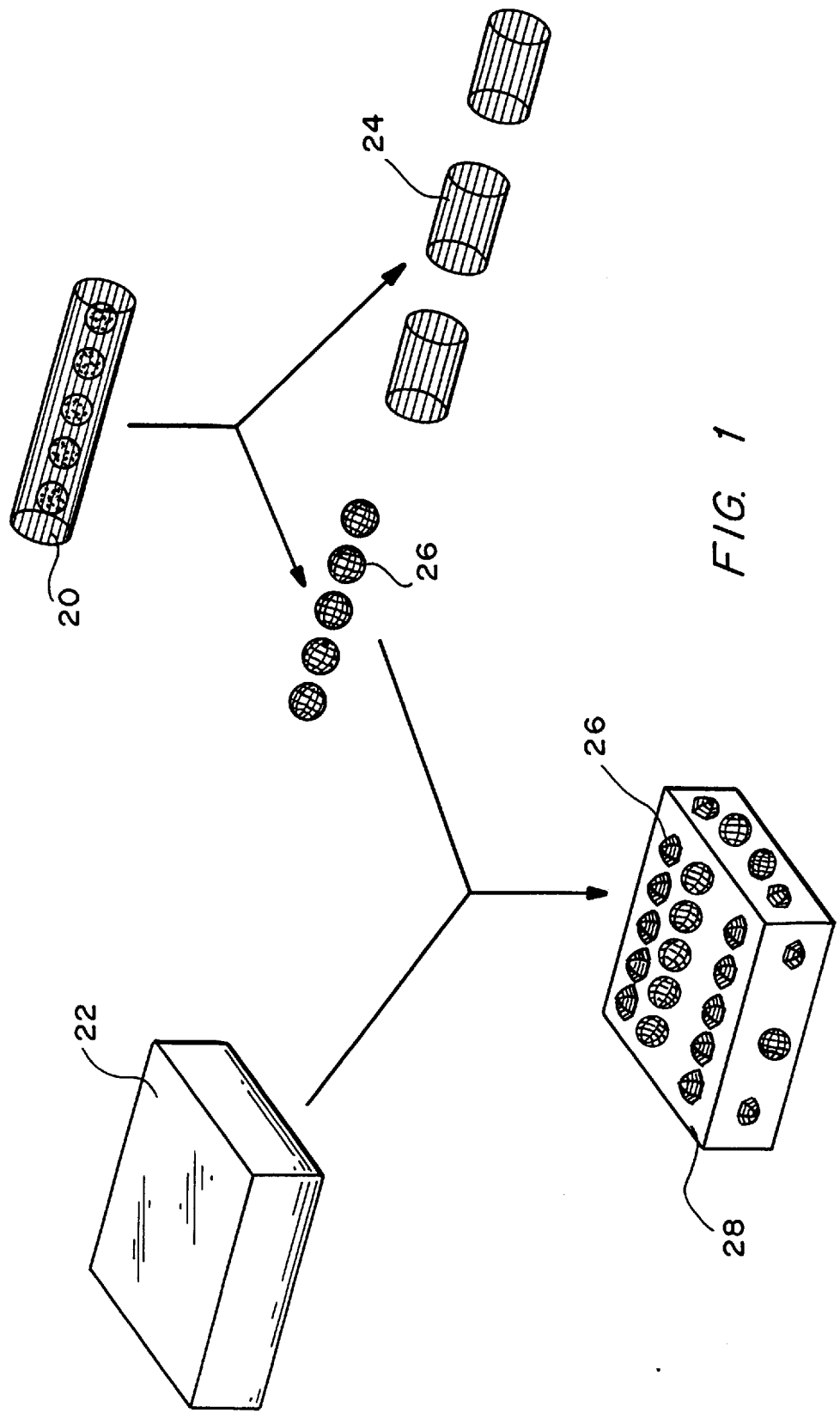

United States Patent [19]
Villeneuve

[11] Patent Number: 5,866,415
[45] Date of Patent: Feb. 2, 1999

[54] MATERIALS FOR HEALING CARTILAGE AND BONE DEFECTS

[76] Inventor: Peter E. Villeneuve, 630 Westview St., Cleveland, Wis. 53015

[21] Appl. No.: 823,565

[22] Filed: Mar. 25, 1997

[51] Int. Cl.⁶ .................................................. C12N 5/00
[52] U.S. Cl. ........................... 435/325; 424/93.7; 623/11; 623/16; 128/898
[58] Field of Search ........................... 435/325; 424/93.7; 623/11, 16; 128/898

[56] References Cited

U.S. PATENT DOCUMENTS

| | | | |
|---|---|---|---|
| 5,516,532 | 5/1996 | Atala | 424/548 |
| 5,655,546 | 8/1997 | Halpern | 128/898 |
| 5,700,289 | 12/1997 | Breitbart et al. | 623/16 |
| 5,713,374 | 2/1998 | Pachene et al. | 128/898 |

FOREIGN PATENT DOCUMENTS

| | | |
|---|---|---|
| 739631 | 10/1996 | European Pat. Off. . |
| 95/30383 | 11/1995 | WIPO . |

OTHER PUBLICATIONS

Brittberg, 1994, Treatment of deep cartilage defects in the knee with autologous chondrocyte transplantation, The new England Journal of Medicine, vol. 331 No. 14 pp. 889.

Skoog, 1976, The formation of articular cartilage from free perichondrial grafts, Plastic & reconstructive Surgery, vol. 57, No. 1 pp. 1.

Rubak, 1982, Chondrogenesis in repair of articular cartilage defects by free periosteal grafts in rabbits, Acta orthop. Scand, vol. 53 pp. 181.

Nakahara, 1990, Culture–expanded periosteal–derived cells exhibit osteochondrogenic potential in porous calcium phospate ceramics in Vivo, Clinical Orthopaedics and Related Research, vol. 276, pp. 291.

*Primary Examiner*—Leon B. Lankford, Jr.
*Attorney, Agent, or Firm*—Arnall Golden & Gregory, LLP

[57] ABSTRACT

The invention concerns methods for the production of in vitro constituted biological materials and their subsequent use as implants for healing cartilage and bone defects. A biological composite (28) comprising periosteum (22) and cartilage or bone forming cells (26) is described as well as an in vitro cultured periosteum.

16 Claims, 1 Drawing Sheet

MATERIALS FOR HEALING CARTILAGE AND BONE DEFECTS

BACKGROUND

1. Field of Invention

This invention relates to the treatment of cartilage and bone defects with biological materials manufactured in vitro. The invention also relates to the methods involved in producing the in vitro constituted biological materials.

2. Description of Prior Art

Over time, cartilage and bone loses the capacity to regenerate itself, making repair of articular cartilage and bone defects very difficult.

Heretofore a wide variety of methods have been proposed and implemented for healing cartilage and bone defects.

One such method for the treatment of cartilage defects consists of mechanically fixing a periosteal flap (bone skin) over the cartilage defect and implanting autologous cultured cartilage forming cells (chondrocytes) under the periosteal flap as described by Brittberg et al. "Treatment of deep cartilage defects in the knee with autologous chondrocyte transplantation," *The New England Journal of Medicine* 331:14, 889–895 (1994). Doctors regard this method as complicated with respect to the mechanical fixation of the periosteal graft and the injection of the cartilage forming cells (chondrocytes). The process requires skills and a considerable amount of practice. The process involves harvesting the periosteal graft from the proximal medial tibia which causes unwanted bleeding into the adjacent knee joint. A percentage of the injected cells are lost due to diffusion. In essence, doctors find the process as described by Brittberg et al. unsatisfactory because it is complicated, requires training, induces unwanted bleeding into the adjacent joint, and does not utilize all of the injected cells.

Other methods designed to treat cartilage defects involve grafting the defect with perichondrial and free periosteal grafts as described by Skoog et al. Skoog T. et al. "The formation of articular cartilage from free perichondrial grafts," *Plastic and reconstructive Surgery* 57:1, 1–6 (1976) and Rubak J. M. et al. "Chondrogenesis in repair of articular cartilage defects by free periosteal grafts in rabbits," *Acta Orthop.* 53:181–186 (1982). However, these techniques are unsatisfactory because they are limited by the amount of tissue available for grafting and the tendency toward ossification of the repair tissue.

Gendler EPO 739631A2 provides a method for producing a biological material comprising reconstituted cartilage tissue. His invention involves growing chondrocytes on a flexible sheet of 1.5 mm thick demineralized natural bone. This system will only demonstrate utility when the bone is non-self-derived because harvesting self-derived bone requires a complicated and painful surgery.

Atala et al. U.S. Pat. No. 5,516,532 provide a method for entrapping bone or cartilage cells in an organic polymer. The organic polymer is not a natural self-derived material which limits its utility. In addition, the cellular composite lacks the mechanical properties that are required for the treatment of cartilage and bone defects.

Barone et al. WO95/30383 propose methods for the production of a synthetic cartilage patch. Chondrocytes are manipulated in vitro to produce an endogenous synthetic matrix. Unfortunately, the synthetic matrix lacks the mechanical properties that are required for the treatment of cartilage defects located in the knee.

Approximately 20% of all bone fractures form a mechanically weak non-union. Repairing non-unions is a slow and painful process that might require three separate operations. Currently, the treatment of non-union bone fractures involves only surgical techniques. Nakahara et al. "Culture-expanded periosteal-derived cells exhibit osteochondrogenic potential in porous calcium phosphate ceramics in vivo," *Clin Orthop* 276:291–298 (1992) have suggested an experimental bone healing material comprising a porous calcium phosphate support and periosteal-derived cells. The system they describe for manufacturing the healing material is extremely complicated and comprises a unnatural synthetic support. The patient must resorb the support which might be associated with unforeseen, unwanted side-effects.

The current cartilage repair techniques require skills and causes bleeding into the knee or involve the use of mechanically weak non-self-derived material. The current bone repair techniques are not effective and time consuming. Therefore, most doctors would find it desirable to have alternative safe methods and materials to streamline and accelerate the treatment of cartilage and bone defects.

OBJECTS AND ADVANTAGES

Accordingly I claim the following as the objects of the invention: to provide biological materials for the safe, efficient, and effective clinical treatment of cartilage and bone defects regardless of the origin or location of the defect.

SUMMARY OF THE INVENTION

A composite material formed of periosteum and cartilage or bone forming cells is cultured in vitro, for implantation into a patient to induce the formation of healthy cartilage or bone tissue in defects that do not normally heal, and/or accelerate the healing process relative to untreated defects.

In addition we claim the following advantages of the invention: treating cartilage and bone defects with the materials according to the invention will require a minimum of skill and training, the materials will induce the formation of healthy cartilage or bone tissue in defects that do not normally heal, the materials will accelerate the healing process relative to untreated defects. Manufacturing the materials described here autologously (self-derived) will avoid disease transmission and the problems associated with rejection.

The reader will find further objects and advantages of the invention from a consideration of the ensuing description and the accompanying drawing.

DRAWING FIGURE

FIG. 1 shows a perspective view of the periosteum composite and the starting materials used to construct the periosteum composite according to the invention.

DRAWING REFERENCE NUMERALS

20 tissue containing cartilage or bone forming cells
22 periosteum
24 discarded acellular tissue
26 cartilage or bone forming cells
28 periosteum composite consisting of periosteum and cartilage or bone forming cells

INVENTION—DESCRIPTION

FIG. 1 shows the periosteum composite and starting materials used to construct the periosteum composite according to the preferred embodiment of the invention. The composite 28 is a combination of periosteum 22 and any one or a combination of cartilage or bone forming cells 26 isolated from naturally occurring tissue(s) 20. The starting materials 20 & 22 maybe non-self-derived or self-derived.

Another form of the invention comprises in vitro cultured periosteum. Whereby the culturing renders the endogenous cells enclosed in the periosteum mitotic and induces subsequent in situ cellular expansion. The cultured periosteum maybe non-self-derived or self-derived (autologous).

APPLICATIONS

The composite 28 and or the cultured periosteum described here is used to heal cartilage and bone defects. The composite 28 and or the cultured periosteum is placed in direct contact with cartilage and bone defects. Defects treated with the biologically active materials will heal faster. The materials increase the chance of complete tissue formation relative to wounds that are not treated with the composite 28 or the cultured periosteum. While I believe the faster more complete healing is directly related to the number of cells 26 attached to the periosteum composite 22 or the number of cells in the cultured periosteum, I do not wish to be bound by this. I also believe the cartilage and bone forming cells which are contained in naturally occurring periosteum 22 communicate with the attached cells 26 to effect a faster and more complete healing, however, I do not wish to be bound by this.

While my above description contains many specificities, these should not be construed as limitations on the scope of the invention, but rather as an exemplification of one preferred embodiment thereof. Many other variations are possible. Those skilled in the art will envision many other possible variations are within its scope. For example, skilled artisans will readily be able to change the dimensions and shapes of the various embodiments. They will also be able to add more material things to the composite of FIG. 1, e.g., they can add adhesive glues or mechanical supports to the periosteum. They could attach cartilage or bone forming cells which are bound in a synthetic matrix or natural tissue to the periosteum with glues or by physical means. The real core of this invention involves activating naturally occurring periosteum by expanding endogenous cells or combining the periosteum with cartilage or bone forming cells independent of the means of attachment and sundry other details. Therefore, the reader is requested to determine the scope of the invention by the appended claims and their legal equivalents, and not by the examples which have been given.

I claim:

1. A biological material for the treatment of cartilage or bone defects, comprising periosteum of sufficient size to accommodate the defect, and cartilage or bone forming cells, wherein the cartilage or bone forming cells are attached to the periosteum in vitro.

2. The biological material of claim 1 wherein the cells or periosteum are isolated from tissue from a patient to be treated.

3. A method for the treatment of cartilage or bone defects comprising implanting at the site to be treated a biological material comprising periosteum of sufficient size to accommodate the defect and cartilage or bone forming cells, wherein the cartilage or bone forming cells are attached to the periosteum in vitro.

4. The method of claim 3 wherein the biological material is cultured in vitro prior to implantation.

5. The method of claim 3 wherein the biological materials is implanted to repair cartilage or bone damaged by inflamation, trauma or aging.

6. A method of producing a biological material comprising periosteum and cartilage or bone forming cells, wherein the method comprises isolating and attaching the cartilage or bone forming cells on periosteum in growth media to produce a bilayer composite characterized by a layer of periosteum and a layer of cartilage or bone forming cells attached to the periosteum.

7. The method of claim 6 wherein said cartilage and bone forming cells are isolated from tissue of a patient to be treated.

8. The biological material of claim 1 produced by isolating and attaching cartilage or bone forming cells on periosteum in growth media to produce a bilayer composite characterized by a layer of periosteum and a layer of cartilage or bone forming cells.

9. The method of claim 3 wherein the biological material is produced by isolating and attaching cartilage or bone forming cells on periosteum in growth media to produce a bilayer composite characterized by a layer of periosteum and a layer of cartilage or bone forming cells.

10. The biological material of claim 1 wherein the biological material is cultured in vitro.

11. The biological material claim 1 wherein the biological material is shaped for the repair of cartilage or bone damaged by inflammation, trauma or aging, or for the repair of cartilage or bone which is congenitally defective.

12. The method of claim 6 further comprising culturing the isolated periosteum in growth media to produce a biological material containing in vitro expanded cells.

13. The method of claim 12 wherein the cells or periosteum is isolated from the tissue of a patient to be treated.

14. The biological material of claim 10 wherein the method further comprises culturing the isolated periosteum in growth media to produce a biological material containing in vitro expanded cells.

15. The biological material of claim 1 containing in vitro expanded periosteal cells.

16. The method of claim 3 wherein the biological material is implanted to repair of cartilage or bone which is congenitally defective.

* * * * *